US00PP28537P2

(12) United States Plant Patent
Thorup

(10) Patent No.: US PP28,537 P2
(45) Date of Patent: Oct. 17, 2017

(54) ***SALVIA* PLANT NAMED 'BALMIRBUR'**

(50) Latin Name: *Salvia greggii*
Varietal Denomination: Balmirbur

(71) Applicant: Ball Horticultural Company, West Chicago, IL (US)

(72) Inventor: Troy Thorup, Chiang Mai (TH)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/330,159

(22) Filed: Aug. 16, 2016

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Audrey Charles

(57) ABSTRACT

A new and distinct cultivar of *Salvia* plant named 'Balmirbur', characterized by its deep red-purple colored flowers, medium green-colored foliage, and moderately vigorous, upright growth habit, is disclosed.

1 Drawing Sheet

Latin name of genus and species of plant claimed: *Salvia greggii.*

Variety denomination: 'Balmirbur'.

BACKGROUND OF THE INVENTION

The present invention relates to a new and distinct cultivar of *Salvia* plant botanically known as *Salvia greggii* and hereinafter referred to by the cultivar name 'Balmirbur'.

The new cultivar originated in a controlled breeding program in Guadalupe, Calif. during July 2013. The objective of the breeding program was the development of *Salvia* cultivars having large flowers and an upright-mounded growth habits.

The new *Salvia* cultivar is the result of self-pollination of the proprietary *Salvia greggii* breeding selection coded 13-2703-4, not patented, characterized by its dark burgundy-colored flowers, medium green-colored foliage, and moderately vigorous, upright growth habit. The new cultivar was discovered and selected as a single flowering plant within the progeny of the above stated self-pollination during July 2014 in a controlled environment in Guadalupe, Calif.

Asexual reproduction of the new cultivar by terminal stem cuttings since July 2014 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balmirbur' as a new and distinct cultivar of *Salvia* plant:

1. Deep red-purple colored flowers;
2. Medium green-colored foliage; and
3. Moderately vigorous, upright growth habit.

Plants of the new cultivar differ from plants of the parent primarily in having a flower color of a different shade of red and in having a shorter plant height.

Of the many commercially available *Salvia* cultivars, the most similar in comparison to the new cultivar is HEATWAVE Blaze Sage 'EGGBEN005', U.S. Plant Pat. No. 24,151. However, in comparison, plants of the new cultivar differ from plants of 'EGGBEN005' in at least the following characteristics:

1. Plants of the new cultivar are taller than plants of 'EGGBEN005';
2. Plants of the new cultivar have darker red-purple colored flowers than plants of 'EGGBEN005'; and
3. Plants of the new cultivar have smaller-sized flowers than plants of 'EGGBEN005'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balmirbur'. The plants were approximately eight-months old and grown in one-gallon containers in a greenhouse in Elburn, Ill. Plants were given one pinch prior to transplant, one pinch two weeks after transplant, and a final pinch four weeks after transplant.

DETAILED BOTANICAL DESCRIPTION

Figure 1:
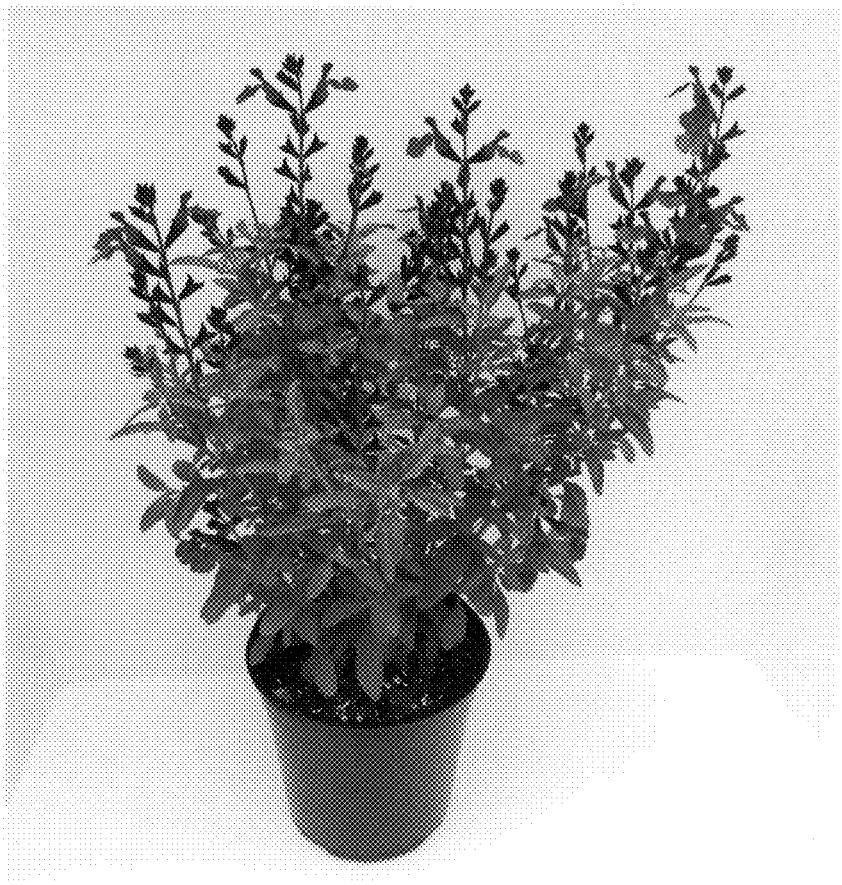
FIG. 1 illustrates a side view of the overall growth and flowering habit of 'Balmirbur'.
Figure 2:
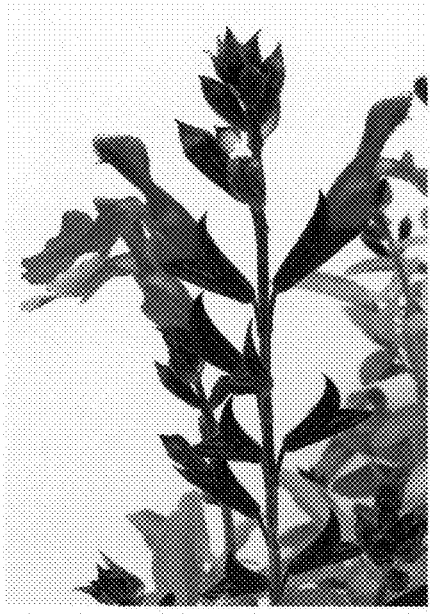
FIG. 2 illustrates a close-up view of an inflorescence of 'Balmirbur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2016 under natural light conditions in West Chicago, Ill.

The following descriptions and measurements describe plants produced from cuttings from stock plants and grown in a glass-covered greenhouse under conditions comparable to those used in commercial practice. The plants were grown utilizing a soilless growth medium in one-gallon containers for approximately seven months in Elburn, Ill. Plants were transplanted in late fall from rooted cuttings and were given one pinch prior to transplant, one pinch two weeks after transplant, and a final pinch four weeks after transplant. Greenhouse temperatures were maintained during the winter months at approximately 45° F. to 65° F. (7.2° C. to 18.3° C.) during the day and approximately 35° F. to 45° F. (1.7° C. to 7.2° C.) during the night. For the final 12 weeks, greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Salvia greggii* cultivar Balmirbur.

Parentage:

*Female and male parent*.—Proprietary *Salvia greggii* breeding selection coded 13-2703-4, not patented.

Propagation:

*Type cutting*.—Terminal stem.

*Time to initiate roots*.—Approximately 10 to 12 days.

*Time to produce a rooted cutting*.—Approximately 35 to 42 days.

*Root description*.—Fine, fibrous white to light brown in color.

*Rooting habit*.—Freely branching.

Plant description:

*Commercial crop time*.—Approximately 8 to 10 weeks from a rooted cutting to finish in a 15 cm pot.

*Growth habit and general appearance*.—Moderately vigorous, upright-mounded growth habit.

*Plant type*.—Subshrub.

*Hardiness*.—USDA zones 7 to 9.

*Size*.—Height from soil level to top of plant plane: Approximately 40.0 cm. Width: Approximately 36.0 cm.

*Branching habit*.—Freely branching. Pinching enhances lateral branching. Quantity of branches per plant: Approximately 3 main basal branches and approximately 9 lateral branches.

*Branch*.—Shape: Square in cross section. Strength: Moderately strong, young growth flexible. Length to base of inflorescence: Approximately 17.0 cm. Diameter: Approximately 3.0 mm. Length of central internode: Approximately 3.5 cm. Texture: Densely pubescent. Color of young stems: 145A. Color of mature stems: 145A, becoming woody 200D with age.

Foliage description:

*General description*.—Quantity of leaves per branch: Approximately 8. Fragrance: Strong, sage-like. Form: Simple. Arrangement: Opposite.

*Leaves*.—Aspect: Acute to perpendicular angle to stem. Shape: Elliptic. Margin: Crenulate. Apex: Broadly acute to rounded. Base: Broadly attenuate to obtuse. Venation pattern: Pinnate. Length of mature leaf: Approximately 5.7 cm. Width of mature leaf: Approximately 2.4 cm. Texture of upper surface: Moderately pubescent. Texture of lower surface: Sparsely pubescent. Color of upper surface of young foliage: 144A and 137A with venation of 144A. Color of lower surface of young foliage: Closest to 138B with venation of slightly lighter than 146D. Color of upper surface of mature foliage: 137B with venation of 146D. Color of lower surface of mature foliage: Closest to 138B with venation of 146D.

*Petiole*.—Length: Approximately 2.0 cm. Diameter: Approximately 1.0 mm. Texture: Moderately pubescent. Color: 146D.

Flowering description:

*Flowering habit*.—'Balmirbur' is freely flowering under outdoor growing conditions blooming from early spring through late summer.

*Lastingness of individual floret*.—Approximately 4 to 5 days.

Inflorescence description:

*General description*.—Type: Raceme with two florets per node, calyx persistent. Quantity of open inflorescences per plant: Approximately 26. Fragrance: Faint, sweet. Length or height of inflorescence: Approximately 9.0 cm to 17.0 cm. Width of inflorescence: Approximately 5.5 cm. Quantity of fully-open flowers per inflorescence: Approximately 2 to 4.

*Peduncle*.—Shape: Square in cross section. Strength: Strong. Aspect: Erect. Length: Approximately 3.0 cm. Diameter: Approximately 2.0 mm. Texture: Densely pubescent. Color: 144A with an overlay of 187A.

Flower description:

*Type*.—Single, zygomorphic.

*Bud*.—Rate of opening: Generally takes 2 to 3 days for bud to progress from first color to fully open flower.

*Bud just before opening*.—Shape: Obovoid. Length: Approximately 1.5 cm. Diameter: Approximately 5.0 mm. Texture: Densely pubescent. Color: Calyx of 145A with a heavy overlay of 187A; petals of N92D with pubescence of 86A.

*Corolla*.—Shape: Bilabiate, lower lip having three lobes, based fused. Width: Approximately 2.0 cm. Length: Approximately 2.3 cm. Depth: Approximately 3.2 cm.

*Upper lip*.—Shape: Hooded. Margin: Entire. Apex: Rounded. Length from throat: Approximately 1.1 cm. Width: Approximately 4.0 mm. Texture of inner surface: Glabrous. Texture of outer surface: Densely pubescent. Color of pubescence: 86A. Color of inner surface when first and fully open: NN155D, translucent. Color of outer surface when first and fully open: 71A.

*Lower lip*.—Shape of central lobe: Orbicular, slightly cupped. Shape of lateral lobes: Elliptic to oblong. Margin of central lobe: Shallowly scalloped. Margin of lateral lobes: Entire. Apex of central lobe: Emarginate. Apex of lateral lobes: Rounded. Length from throat of central lobe: Approximately 1.8 cm. Width of central lobe: Approximately 2.0 cm. Length from throat of lateral lobes: Approximately 9.0 mm. Width of lateral lobes: Approximately 4.0 mm. Texture of upper surface: Glabrous. Texture of lower surface: Sparsely pubescent. Color of upper surface when first and fully open: Closest to 60A. Color of lower surface when first and fully open: Closest to 60B with 71B at base.

*Corolla tube*.—Length: Approximately 2.1 cm. Width: Approximately 8.0 mm. Texture of inner and outer surfaces: Glabrous. Color of inner surface: NN155D, translucent. Color of outer surface: 71A with 72A.

*Calyx*.—Shape: Tubular. Length: Approximately 1.6 cm. Diameter: Approximately 9.0 mm.

*Sepals*.—Quantity per flower: 4, fused. Shape: Obovate. Margin: Entire. Apex: Acuminate. Length: Approximately 1.6 cm. Width: Two of approximately 4.0 mm and one of approximately 7.0 mm. Texture of inner and outer surface: Densely pubescent. Color of inner surface: 145A with an overlay of 187A at apex. Color of outer surface: 145A with a heavy overlay of 187A.

*Bracts*.—Quantity: One bract located at the base of each developing floret, bracts abscise as florets mature. Length: Approximately 9.0 mm. Width: Approximately 4.0 mm. Texture of inner surface: Glabrous. Texture of outer surface: Densely pubescent. Color of inner surface: NN155D with N186D at tip. Color of outer surface: Closest to N186D with base of NN155D and 187A at tip.

*Pedicel*.—Strength: Strong, flexible. Aspect: At an acute angle. Length: Approximately 5.0 mm. Diameter: Approximately 1.0 mm. Texture: Densely pubescent. Color: 145A with an overlay of N186B.

*Reproductive organs*.—Androecium: Stamen quantity: 2 per flower, dorsifixed, strongly curved. Stamen length: Approximately 1.5 cm. Filament length: Approximately 1.4 cm. Filament color: NN155D with an overlay of 77A in center, opaque. Anther shape: Narrowly elliptic to oblong. Anther length: Approximately 2.0 mm. Anther color: N187D. Pollen amount: Abundant. Pollen color: 9A. Gynoecium: Pistil quantity: 1 per flower, strongly curved. Pistil length: Approximately 3.2 cm. Stigma shape: Cleft, two-parted. Stigma length: 4.0 mm. Stigma color: 86A. Style length: Approximately 2.6 cm. Style color: NN155D, opaque with an overlay of 86B near stigma. Style texture: Glabrous with a vertical line of feather-like pubescence extending from the stigma for approximately 7.0 mm. Ovary length: Approximately 2.0 mm. Ovary color: 154D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balmirbur', substantially as herein illustrated and described.

* * * * *